(12) United States Patent
Rassouli

(10) Patent No.: US 11,801,350 B2
(45) Date of Patent: Oct. 31, 2023

(54) QUICK-CONNECT SYRINGE AND NEEDLE SYSTEM

(71) Applicant: Arash Anthony Rassouli, Huntington Beach, CA (US)

(72) Inventor: Arash Anthony Rassouli, Huntington Beach, CA (US)

( * ) Notice: Subject to any disclaimer, the term of this patent is extended or adjusted under 35 U.S.C. 154(b) by 146 days.

(21) Appl. No.: 16/208,147

(22) Filed: Dec. 3, 2018

(65) Prior Publication Data

US 2019/0167911 A1 Jun. 6, 2019

Related U.S. Application Data

(60) Provisional application No. 62/594,501, filed on Dec. 4, 2017.

(51) Int. Cl.
*A61M 5/34* (2006.01)
*A61M 5/31* (2006.01)
*A61M 5/32* (2006.01)
*A61M 39/10* (2006.01)

(52) U.S. Cl.
CPC .......... *A61M 5/343* (2013.01); *A61M 5/3134* (2013.01); *A61M 5/3293* (2013.01); *A61M 5/345* (2013.01); *A61M 5/347* (2013.01); *A61M 5/348* (2013.01); *A61M 2039/1027* (2013.01)

(58) Field of Classification Search
CPC ...... A61M 5/343; A61M 5/345; A61M 5/347; A61M 5/3293; A61M 5/3134; A61M 5/348; A61M 2039/1027
See application file for complete search history.

(56) References Cited

U.S. PATENT DOCUMENTS

| 3,469,581 | A | | 9/1969 | Burke |
| 4,449,539 | A | | 5/1984 | Sarstedt |
| 4,664,656 | A | * | 5/1987 | Taddei .................... A61M 5/24 604/241 |
| 5,725,508 | A | | 3/1998 | Chanoch et al. |

(Continued)

FOREIGN PATENT DOCUMENTS

| GB | 292032 | 6/1928 |
| IT | 1222331 | 9/1990 |

*Primary Examiner* — Lauren P Farrar
*Assistant Examiner* — Hamza A Darb
(74) *Attorney, Agent, or Firm* — John Rizvi; John Rizvi, P.A.—The Patent Professor®

(57) ABSTRACT

A quick-connect syringe and needle system is provided including a syringe having a threaded portion, a needle assembly having a needle body and a needle affixed to the needle body and an intermediate adapter engageable with the syringe and releasably engageable with the needle body. A quick-connect mechanism is provided on the needle body and intermediate adapter for quickly and easily connecting the needle assembly with the syringe and intermediate adapter. The quick-connect mechanism can include a pair of diametrically opposed L-shaped slots formed in a rear portion of the needle body and a pair of corresponding and diametrically opposed projections extending from a front or locking portion of the intermediate adapter. The needle assembly is attached to the intermediate adapter by inserting the projections into the slots and giving the assembly a quick quarter turn to firmly seat the projections within the slots.

13 Claims, 13 Drawing Sheets

(56) References Cited

U.S. PATENT DOCUMENTS

| | | | |
|---|---|---|---|
| 7,063,673 B2 * | 6/2006 | Marsden | A61M 5/347 600/576 |
| 8,012,132 B2 | 9/2011 | Lum et al. | |
| 2002/0138045 A1 | 9/2002 | Moen | |
| 2003/0216695 A1 | 11/2003 | Yang | |
| 2007/0016140 A1 | 1/2007 | Berler | |
| 2007/0173776 A1 | 7/2007 | Caizza et al. | |
| 2010/0217206 A1 | 8/2010 | Lum et al. | |
| 2011/0125130 A1 | 5/2011 | Schraga | |
| 2017/0232208 A1 * | 8/2017 | Evans | A61M 5/348 604/243 |

* cited by examiner

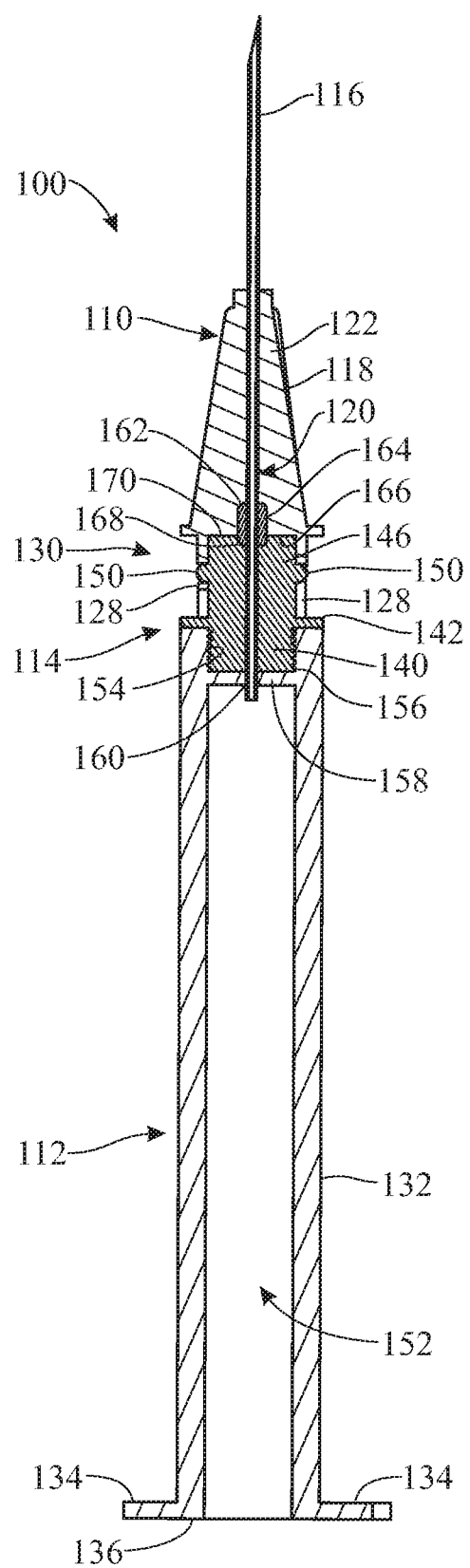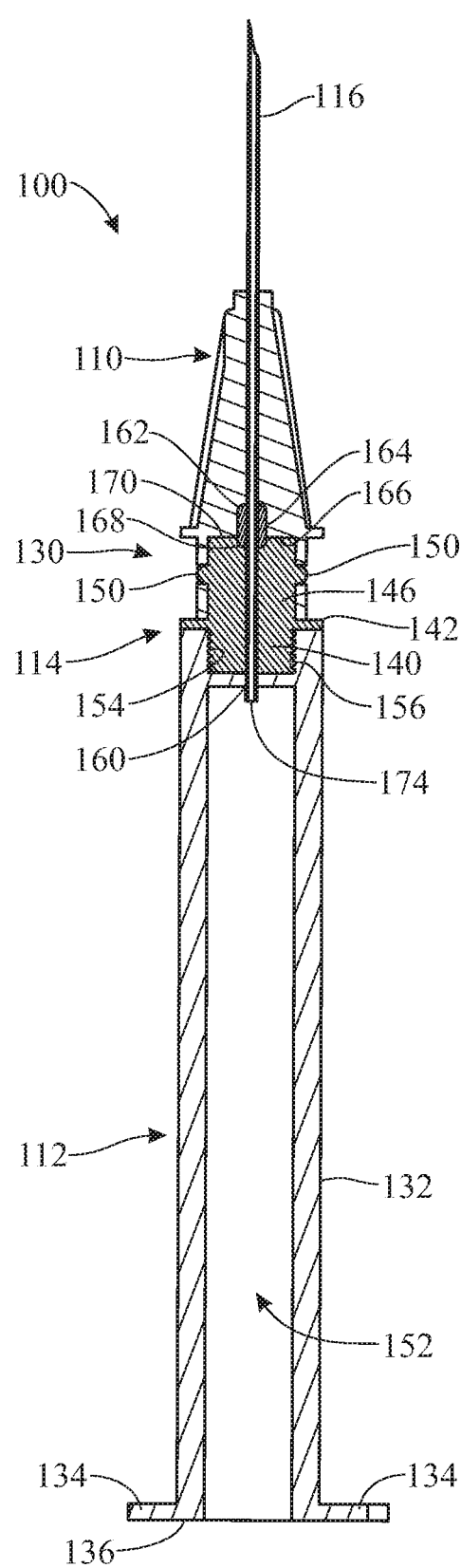

QUICK-CONNECT SYRINGE AND NEEDLE SYSTEM

CROSS REFERENCE TO RELATED APPLICATION

This application claims the benefit of U.S. Provisional Patent Application Ser. No. 62/594,501, filed on Dec. 4, 2017, which is incorporated by reference herein in its entirety.

FIELD OF THE INVENTION

The present invention relates generally to syringe and needle systems, and more particularly, to a quick-connect syringe and needle system comprising a mechanism to quickly and easily connect a needle assembly to a syringe.

BACKGROUND OF THE INVENTION

It is important in many surgical procedures to utilize a needle and syringe system to inject various medical materials or compounds into a patient. Typical compounds may include saline solutions, anesthetics, anti-coagulants, antibiotics, etc. Often, multiple injections are required during a single treatment or procedure.

Syringes are typically hollow and can accept the various compounds directly, either as loose fluid or in breakable or pierceable containers, or by inserting the attached needle into a container holding the compound and drawing it up into the syringe with a typical piston/plunger arrangement. When multiple injections are required, it is often desirable or even necessary to utilize a new and sterilized needle to avoid complications or issues such as, for example, cross-contamination, infection, etc. Additionally, once the needle is removed from the syringe, the syringe may need to be sterilized prior to reuse.

Typically, removal of an existing used needle or needle assembly from a syringe requires unthreading the needle or needle assembly from the syringe by turning or twisting it in at least one 360° rotation to separate the threads which connect the needle assembly to the syringe. This can be a time consuming and inconvenient task during the heat of a surgery.

Many times, due to stress or other undesired factors, the person in charge of exchanging the used needle for a new sterilized needle will attempt to simply and forcibly pull the needle assembly and syringe apart or try to twist or pry off the needle assembly for faster removal. Unfortunately, this can cause the person to get pricked by the needle and risk infection, as well as damage the syringe making it necessary to get an entire new syringe and needle assembly.

Accordingly, there is an established need for a time-saving syringe and needle assembly or system that solves at least one of the aforementioned problems. For example, a syringe and needle assembly is desired which allows a surgeon or attendant to quickly, safely and conveniently remove the needle assembly from the syringe, connect the needle assembly to the syringe, or replace the needle assembly provided on the syringe.

SUMMARY OF THE INVENTION

The present invention is directed to a quick-connect syringe and needle system that is capable of quickly and easily exchanging a needle assembly with a syringe by a simple turn motion and without having to bend or break off the needle assembly from the syringe. The quick-connect syringe and needle system can include a syringe, an intermediate adapter connectable to the syringe, and a needle assembly having a needle body and a needle extending through the needle body. The needle body and the intermediate adapter together form a quick-connect mechanism for releasable engagement therebetween. The quick-connect mechanism can include one or more slots, and more preferably a pair of diametrically opposed L-shaped slots, formed in a rear portion of the needle body and a corresponding one or more, and preferably a pair of diametrically opposed, projections extending from a front or locking body portion of the intermediate adapter. The projections are received in releasable locking engagement within the slots to quickly and easily connect the needle assembly with the intermediate adapter and syringe with a simple turn of the needle assembly relative to the intermediate adapter, the turn preferably being of approximately 90 degrees. The quick-connect syringe and needle system can be applied to various dental and/or medical syringes, such as, but not limited to, metallic dental syringes configured to receive a needle assembly and extract an anesthetic or other product from a carpule, or plastic medical syringes.

In a first implementation of the invention, a quick-connect syringe and needle system comprises a syringe, a needle assembly and an intermediate adapter. The needle assembly includes a needle assembly body and a needle affixed to the needle assembly body. The needle assembly body has a rear portion defining at least one slot. The intermediate adapter, in turn, is engageable with the syringe to secure the intermediate adapter to the syringe, and includes at least one projection releasably engageable with the at least one slot in the rear portion of the needle assembly body to disconnectably secure the intermediate adapter to the needle assembly. The quick-connect and needle system is configured to adopt an assembled configuration in which the intermediate adapter is secured to the syringe. Furthermore, in the assembled configuration, the intermediate adapter is disconnectably secured to the needle assembly by engagement of the at least one projection of the intermediate adapter with the at least one slot of the rear portion of the needle assembly body of the needle assembly.

In a second aspect, the rear portion of the needle assembly body can include a slotted sleeve which fits over a front portion of the intermediate adapter when the quick-connect and needle system is arranged in the assembled configuration.

In another aspect, the at least one slot can be defined through the slotted sleeve.

In another aspect, the at least one slot can be L-shaped.

In another aspect, the L-shaped slot can include a first slot segment having an open end, and a second slot segment extending from the first slot segment and including a closed end.

In yet another aspect, the first slot segment of the L-shaped slot can be parallel to a longitudinal axis of the needle assembly.

In another aspect, the second slot segment of the L-shaped can be circumferential about the longitudinal axis.

In another aspect, the at least one projection of the intermediate adapter can include two projections and the at least one slot defined in the rear portion of the needle assembly body can include two slots. The two projections can be configured to engage with the two slots.

In another aspect, the two projections can be diametrically opposed to each other, and the two slots can also be diametrically opposed to one another.

In another aspect, the intermediate adapter can be engageable with the syringe in a disconnectable manner.

In yet another aspect, the intermediate adapter can include a threaded portion disconnectably threadable to a forward threaded portion of the syringe.

In another aspect, the intermediate adapter can include a through bore. When the quick-connect and needle system is arranged in the assembled configuration, the needle of the needle assembly can extend through the through bore of the intermediate adapter and into the syringe.

In another aspect, the intermediate adapter may include a radially-protruding collar configured to rest on a front face of the syringe.

In another aspect, the intermediate adapter may comprise an outer wall disposed circumferentially about a longitudinal axis of the intermediate adapter. The outer wall can have an outer texture or shape facilitating manual application of a torque on the outer wall and needle assembly to rotate the needle assembly and intermediate adapter relative to one another for engaging the at least one projection of the intermediate adapter with the at least one slot of the rear portion of the needle assembly body of the needle assembly.

In yet another aspect, when the quick-connect and needle system is arranged in the assembled configuration, the outer wall of the intermediate adapter can be disposed radially outward of the rear portion of the needle assembly body.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which:

FIG. 3 presents a cross-sectional, front elevation view of the quick-connect syringe and needle system of FIG. 1 with a needle assembly and intermediate adapter of the quick-connect syringe and needle system in a first state;

FIG. 4 presents a cross-sectional, front elevation view of the quick-connect syringe and needle system of FIG. 1 with the needle assembly and intermediate adapter in a second state;

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward a quick and easy mechanism for attaching a needle assembly to a syringe utilizing an intermediate adapter that is threaded to the syringe and includes a pair of projections to releasably engage corresponding slots formed on the needle assembly.

Figure 1:
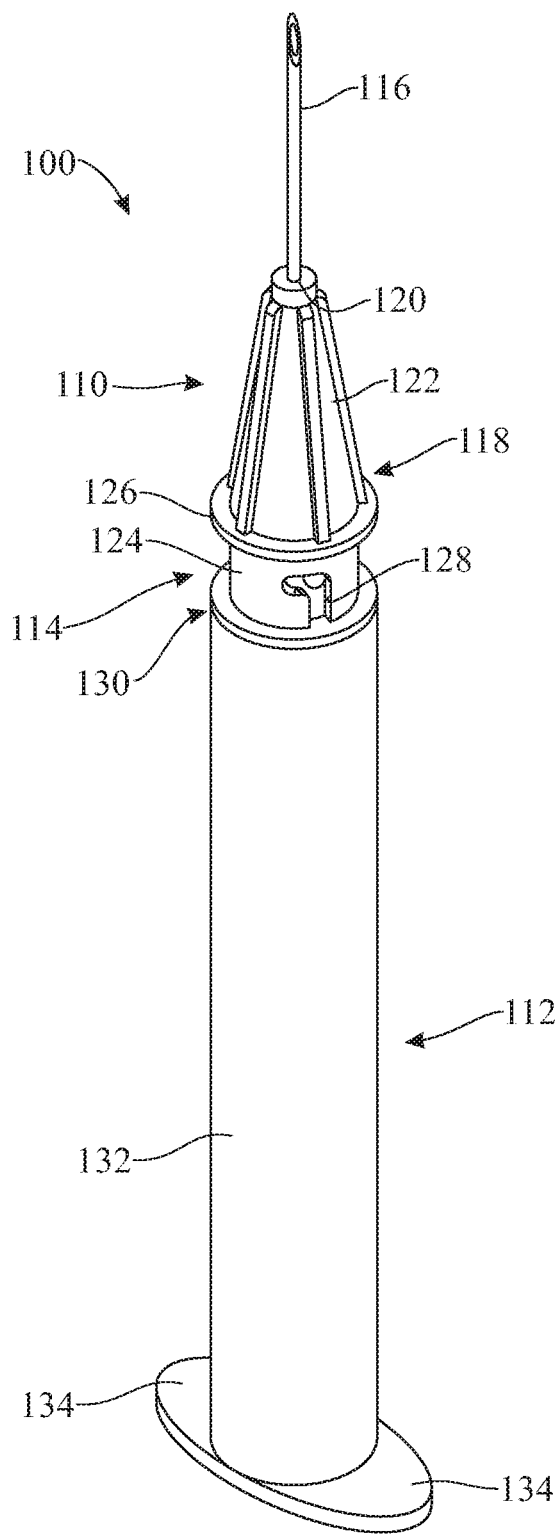
FIG. 1 presents a top front isometric view of a quick-connect syringe and needle system in accordance with a first illustrative implementation of the present invention.
Figure 2:
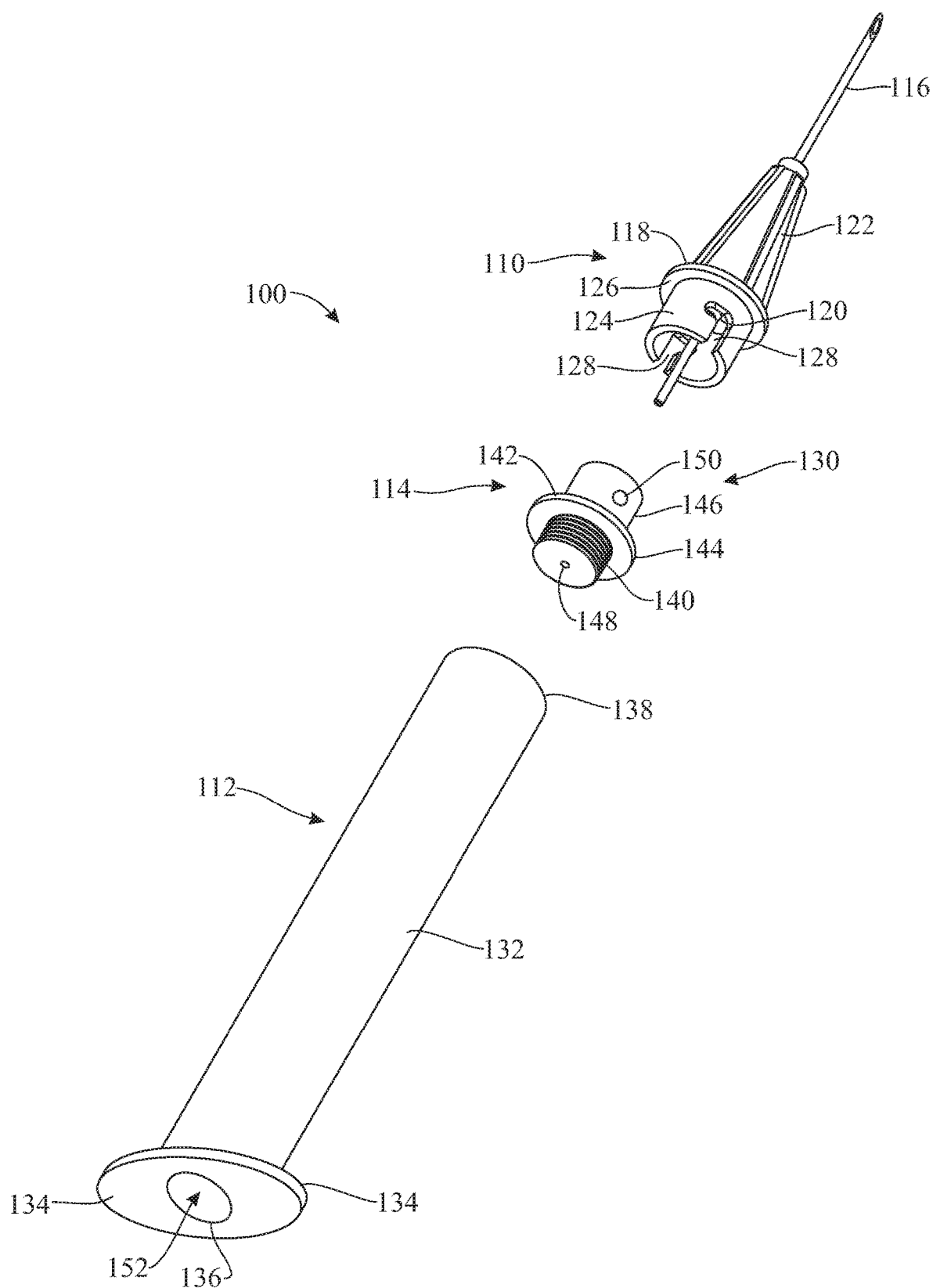
FIG. 2 presents a bottom side isometric view, with parts separated, of the quick-connect syringe and needle system of FIG. 1.

Referring initially to FIGS. 1 and 2, a quick-connect syringe and needle system 100 is illustrated in accordance with a first exemplary embodiment of the present invention, configured as a multi-component needle system. As shown, the quick-connect syringe and needle system 100 generally includes a needle assembly 110, a hollow syringe 112 and an intermediate adapter 114 for quickly and easily attaching and removing the needle assembly 110 from the hollow syringe 112. It should be noted that the hollow syringe 112 may be provided with a piston and plunger assembly (not shown) as is commonly known in the art to draw into and eject compounds from the syringe 112 towards and through the needle assembly 110.

As shown in FIGS. 1 and 2, the needle assembly 110 includes a hollow needle 116 and a needle assembly body 118. The needle 116 extends through, and is secured within, a through bore 120 formed through the needle assembly body 118 (see also FIG. 3). The needle assembly body 118 includes a finned and tapered forward portion 122, a rear portion or slotted rear sleeve 124 and a radially-protruding flange or collar 126 positioned between the forward portion 122 and the slotted rear sleeve 124. The slotted rear sleeve 124 includes one or more L-shaped slots 128, and more preferably a pair of L-shaped slots 128, which, together with the intermediate adapter 114, form part of a quick-connect mechanism 130 for quickly and easily attaching and removing the needle assembly 110 from the syringe 112. Preferably, the pair of L-shaped slots 128 are diametrically opposed to each other through the slotted rear sleeve 124.

The syringe 112 generally includes a hollow syringe body 132 having a pair of finger grasping flanges 134 adjacent an open rear end 136 of the syringe body 132. The syringe body also has an open front end 138 for receipt of the intermediate adapter 114 as described in more detail hereinbelow.

Referring now to FIGS. 2-4, the intermediate adapter 114 includes a rear or threaded body portion 140 which forms a part of a body 142 of the intermediate adapter 114. The body 142 of the intermediate adapter 114 additionally includes a radially-protruding flange or collar 144 and a front or locking body portion 146 extending frontward from the collar 144. A through bore 148 extends through the body 142 of the intermediate adapter 114 for passage of the needle 116 therethrough and into the syringe body 132. One or more, and preferably a pair of, projections 150 are formed on and extend radially outwardly from the locking body portion 146 and are provided to engage the corresponding L-shaped slots 128 formed in the slotted rear sleeve 124 of the needle assembly 110. The projections 150 are preferably diametrically opposed to each other around the locking body portion 146 and may be cylindrical, rectangular, nub like or semicircular, etc., as long as the shape allows them to navigate the L-shaped slots 128 as will be described hereinafter. The locking body portion 146 and projections 150, along with the slotted rear sleeve 124 of the needle assembly 110, together form the aforementioned quick-connect mechanism 130.

Figure 5:
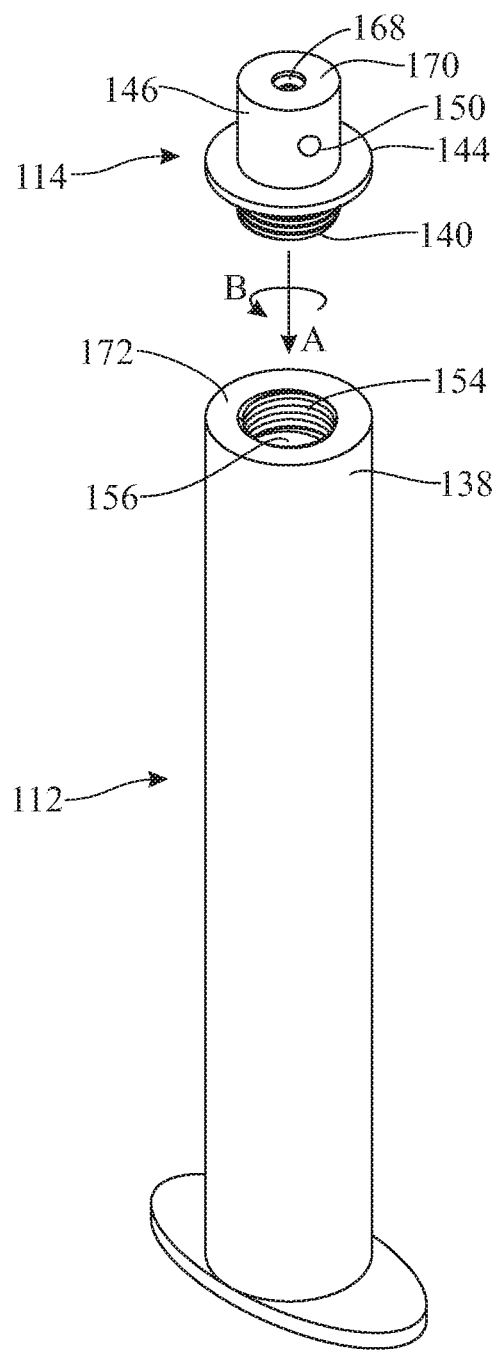
FIG. 5 presents a top front isometric view of a syringe and the intermediate adapter of the quick-connect syringe and needle system of FIG. 1 prior to assembly.

Referring to FIGS. 3-5, the syringe 112 includes a hollow interior 152. As best shown in FIG. 3, in order to attach the intermediate adapter 114 to the syringe 112, the syringe 112 is formed with an interior thread 154 in a recessed portion 156 of the syringe adjacent the open front end 138 of the syringe 112. A partition 158 is formed in the syringe 112 between the recessed portion 156 and the hollow interior 152 and includes a through hole 160 for passage of the needle into the hollow interior 152.

In order to ensure a complete seal between the intermediate adapter 114 and the needle assembly body 118 about the needle 116, a seal 162 can be provided in a recess 164 formed in a rear end face 166 of the tapered forward portion 122 of the needle assembly body 118 and in a recess 168 formed in a front end face 170 of the locking body portion 146 of the intermediate adapter 114.

The disclosed components of the quick-connect syringe and needle system 100 may be formed from a variety of preferably bio-compatible materials commonly used in the art. For example, the needle 116 may be formed from a stainless steel while the needle assembly body 118 may be formed from a polymeric material. The syringe 112 and the intermediate adapter, in whole or in part, may also be formed from a metallic, polymeric or combination of metallic and polymeric materials, glass and combinations thereof, for instance and without limitation.

Referring now to FIGS. 3-8, and initially with regard to FIG. 5, the assembly of the quick-connect syringe and needle system 100, incorporating the quick-connect mechanism 130, will now be described. Initially, the intermediate adapter 114 is positioned adjacent the open front end 138 of the syringe 112. The intermediate adapter 114 is then moved longitudinally, i.e. in direction of arrow A, such that the threaded body portion 140 of the intermediate adapter 114 engages the interior thread 154 in the open front end 138 of the syringe 112. Thereafter, the intermediate adapter 114 is rotated counter-clockwise (in this embodiment) in the direction of arrow B to thread or screw the intermediate adapter 114 into secure connection with the interior thread 154 of the syringe 112. The threaded body portion 140 of the intermediate adapter 114 is continued to be threaded into the interior thread 154 of the syringe 112 until the collar 144 of the intermediate adapter 114 firmly seats against a front face 172 of the syringe 112, thus reaching a seated, assembled position shown in FIG. 6. This assembled position formed by the syringe 112 and intermediate adapter 114 places them in condition for receipt of the needle assembly 110 in quick-connect fashion.

Figure 6:
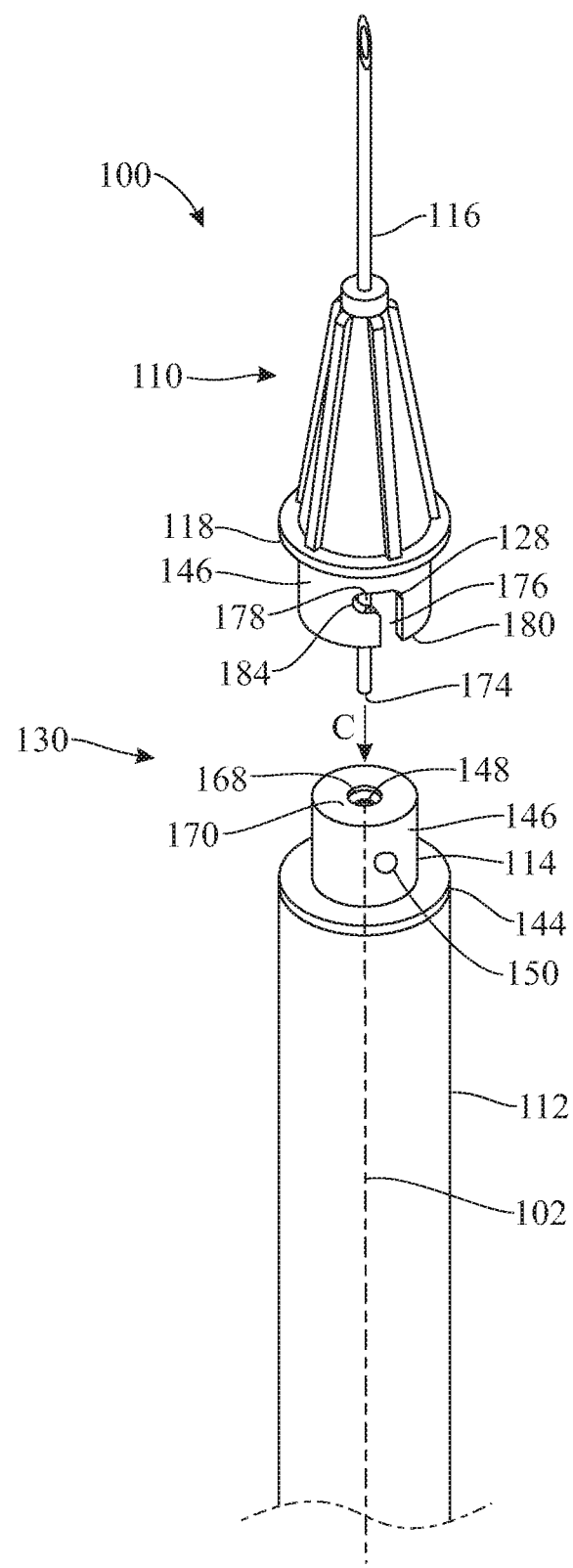
FIG. 6 presents a partial, top front isometric view of the needle assembly of the quick-connect syringe and needle system of FIG. 1 prior to being connected to the assembled intermediate adapter and syringe.

Next, as shown in FIG. 6, in order to attach the needle assembly 110 to the assembled syringe 112 and intermediate adapter 114, the needle assembly 110 is advanced toward the intermediate adapter 114 in the direction of arrow C, i.e. longitudinally, such that a rear end 174 of the needle 116 enters the recess 168 formed in the locking body portion 146 of the intermediate adapter 114 and enters the through bore 148 formed through the intermediate adapter 114. The needle assembly 110 continues to be advanced toward the intermediate adapter 114 until the rear end 174 of the needle 116 passes into the hollow interior 152 of the syringe body 132 (FIG. 4). As noted above, at this point, as shown in FIG. 3, the rear end face 166 of tapered forward portion 122 is flush with the front end face 170 of the intermediate adapter 114.

As the needle assembly 110 is moved in the direction of arrow C, the projections 150 on the locking body portion 146 of the intermediate adapter 114 are aligned with and enter the L-shaped slots 128 formed in the slotted rear sleeve 124 of the needle assembly body 118. The L-shaped slots 128 include a first slot segment 176 open at a rear end 180 of the slotted rear sleeve 124 and a second slot segment 178 extending from an upper end 182 of the first slot segment 176 and at an angle with the first slot segment 176. The first slot segment 176 is preferably parallel to a longitudinal axis 102 of the quick-connect syringe and needle system 100 while the second slot segment 178 is transverse, and preferably perpendicular, to the longitudinal axis 102.

The quick-connect mechanism 130 is operated by aligning the projections 150 on the intermediate adapter 114 with the first slot segments 176 on the needle assembly 110 and moving the needle assembly 110 and the assembled syringe 112 and intermediate adapter 114 together such that the projections 150 enter the first slot segments 176. As noted, the first slot segments 176 are open at the rear end 180 of the slotted rear sleeve 124. The needle assembly 110 is then continued to be pressed together with the intermediate adapter 114 in the direction of arrow C moving the projections 150 longitudinally up through the first slot segments 176 until the projections 150 reach the upper end 182 of the first slot segments 176 and are aligned with the second slot segment 178 in a first state as best shown in FIG. 7 (see also FIG. 3).

Figure 7:
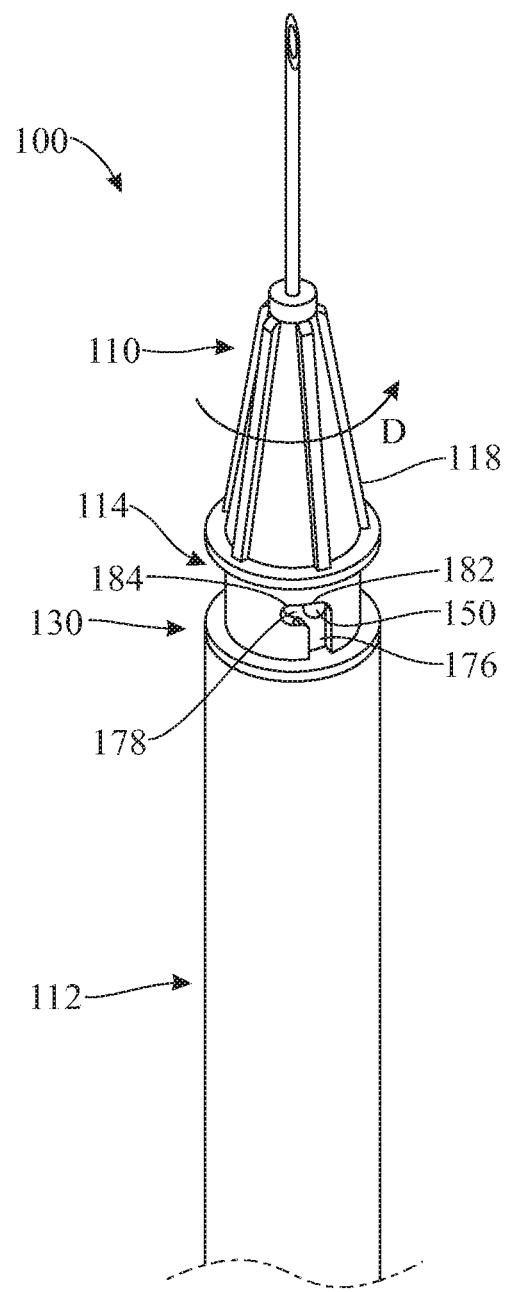
FIG. 7 presents a partial, top front isometric view with the needle assembly of the quick-connect syringe and needle system of FIG. 1 in a first state, as it is being connected to the intermediate adapter.
Figure 8:
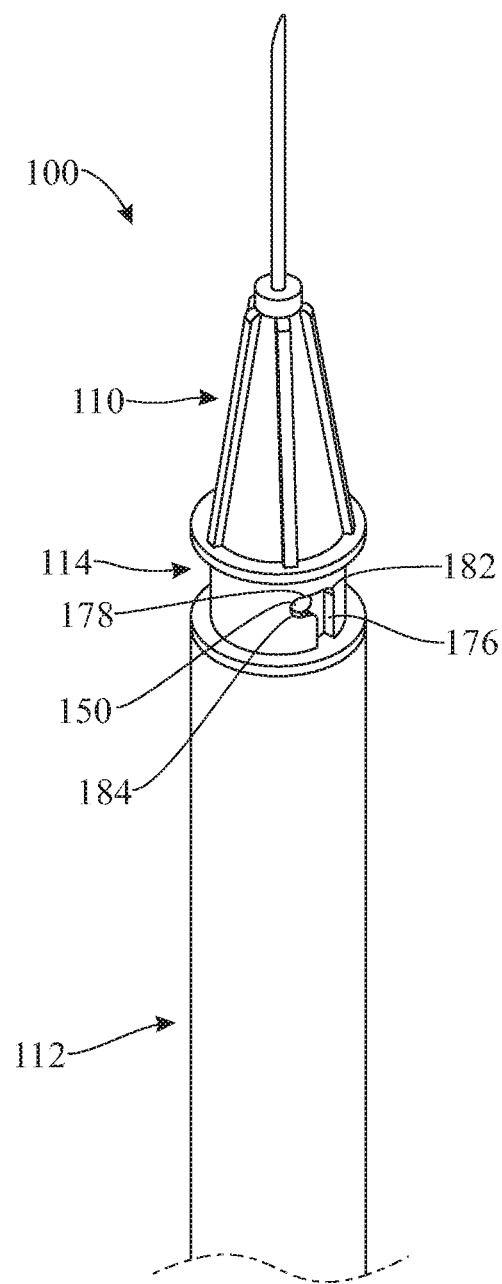
FIG. 8 presents a partial, top front isometric view with the needle assembly of the quick-connect syringe and needle system of FIG. 1 in a second state, fully connected to the intermediate adapter.

With reference to FIGS. 7 and 8, once the projections 150 have reached the first state in the upper end 182 of the first slot segments 176, the operation of the quick-connect mechanism 130 is completed by rotating the needle assembly 110 counter-clockwise in the direction of arrow D (FIG. 7) to move the projections 150 through the second slot segments 178 until the projections 150 reach closed ends 184 of the second slot segments 178 and thus achieve a second state, as shown in FIGS. 8 and 4. This completes the operation of the quick-connect mechanism 130 to easily and releasably secure the needle assembly 110 to the syringe 112 via the intermediate adapter 114. Preferably, the second slot segments 178 have a length which requires the user to rotate the needle assembly 110 ninety degrees relative to the intermediate adapter 114 in order to move the projections 150 from the upper end 182 of the first slot segment 176 to the closed end 184 of the second slot segment 178. This provides an extremely simple and intuitive, yet robust and secure, locking mechanism.

In order to remove the needle assembly 110 from the syringe 112, the above process is reversed moving the projections 150 on the locking body portion 146 of the intermediate adapter 114 back through the second slot segments 178 and first slot segments 176 of the L-shaped slots 128 in the slotted rear sleeve 124 of the needle assembly body 118 to allow the needle assembly 110 to be pulled free of the syringe 112. Thereafter, a new needle assembly 110 may be chosen and attached the syringe 112 by use of the disclosed quick-connect mechanism 130.

Thus, the disclosed quick-connect syringe and needle system 100 provides a quick and easy device and method of exchanging a needle on a syringe without having to break the needle during the exchange. The system can be applied to various dental and/or medical syringes, such as metallic dental syringes configured to receive a needle assembly and extract an anesthetic or other product from a carpule, or plastic medical syringes, for instance and without limitation.

The illustrations of FIGS. 9-14 show a quick-connect syringe and needle system 200 in accordance with a second exemplary embodiment of the invention. Like features of the quick-connect syringe and needle system 200 and the quick-connect syringe and needle system 100 (FIGS. 1-8) are numbered the same except preceded by the numeral '2'. As shown for instance in the assembled configuration view of FIG. 9, similarly to the previous embodiment, the quick-connect syringe and needle system 200 of the present embodiment comprises a needle assembly 210, a syringe 212 (only partially illustrated), and an intermediate adapter 214 configured to facilitate a quick connection of the needle assembly 210 to the syringe 212. The needle assembly 210, syringe 212 and intermediate adapter 214 are formed and mounted along a longitudinal axis 202.

Figure 9:
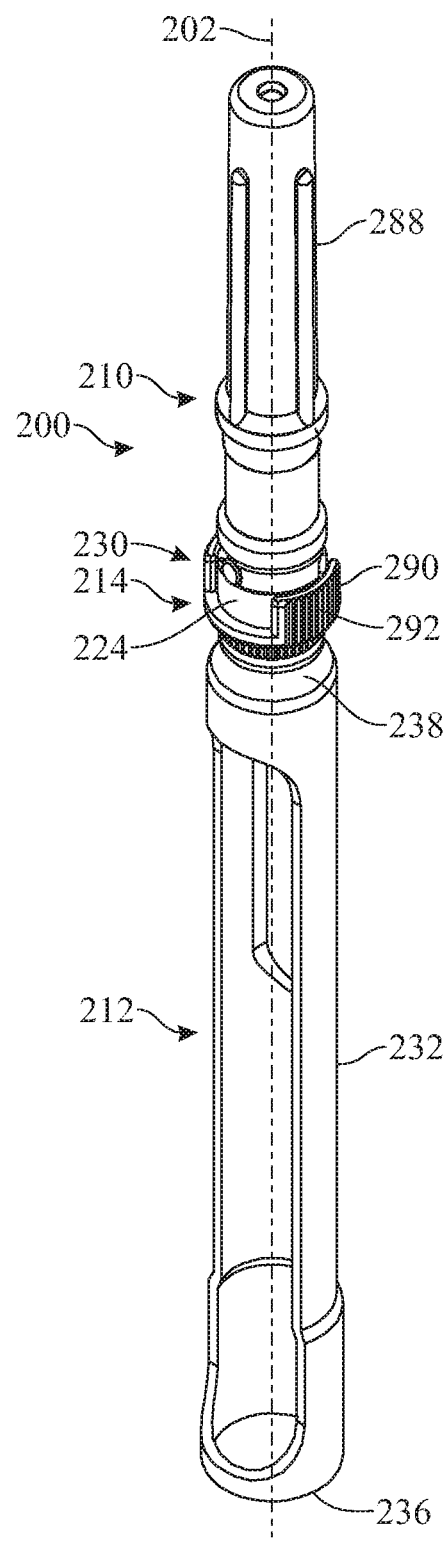
FIG. 9 presents a top front isometric view of a quick-connect syringe and needle system in accordance with a second illustrative implementation of the present invention, wherein the system is shown in an assembled configuration.
Figure 10:
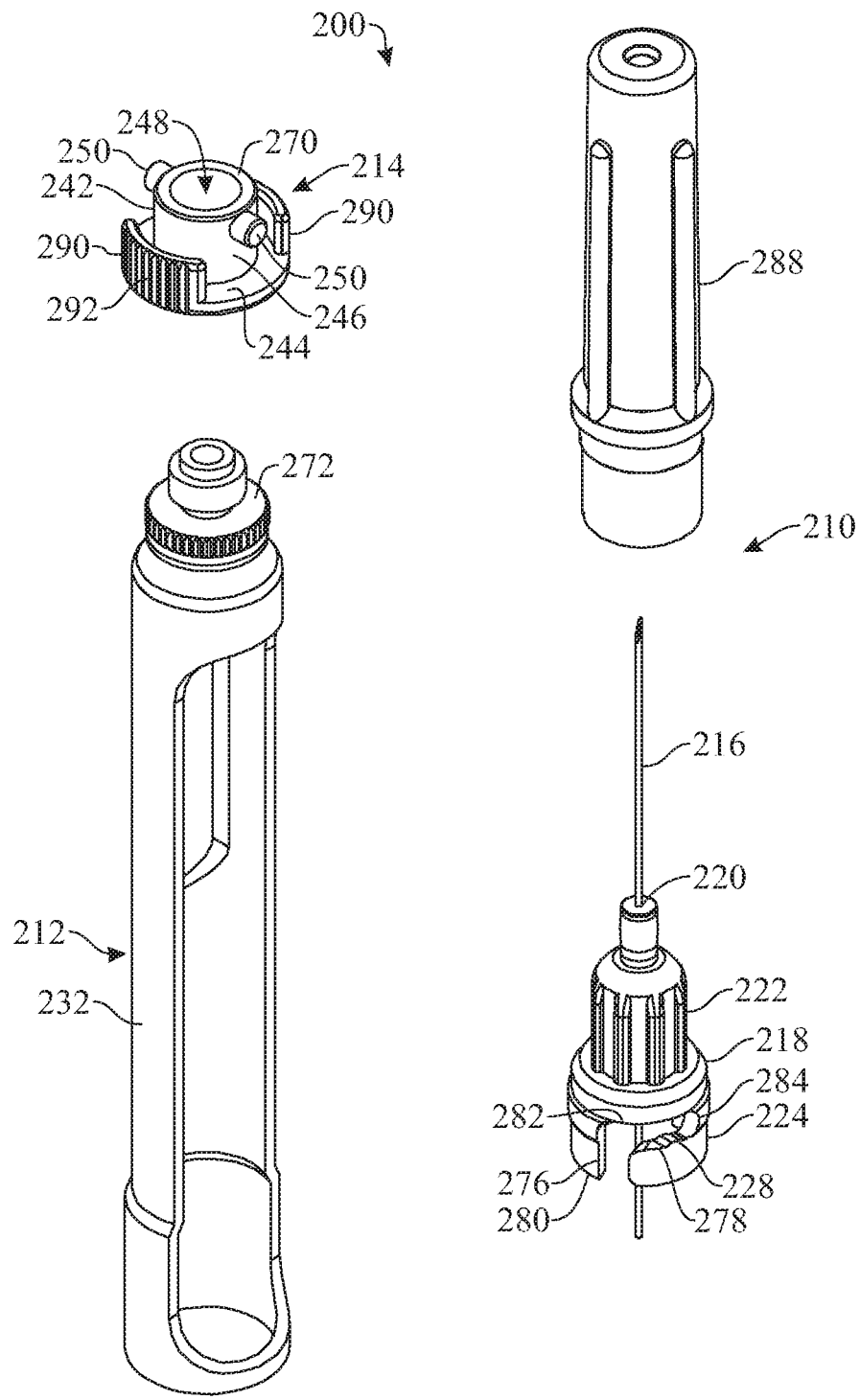
FIG. 10 presents an exploded, top front isometric view of the quick-connect syringe and needle system of FIG. 9.
Figure 11:
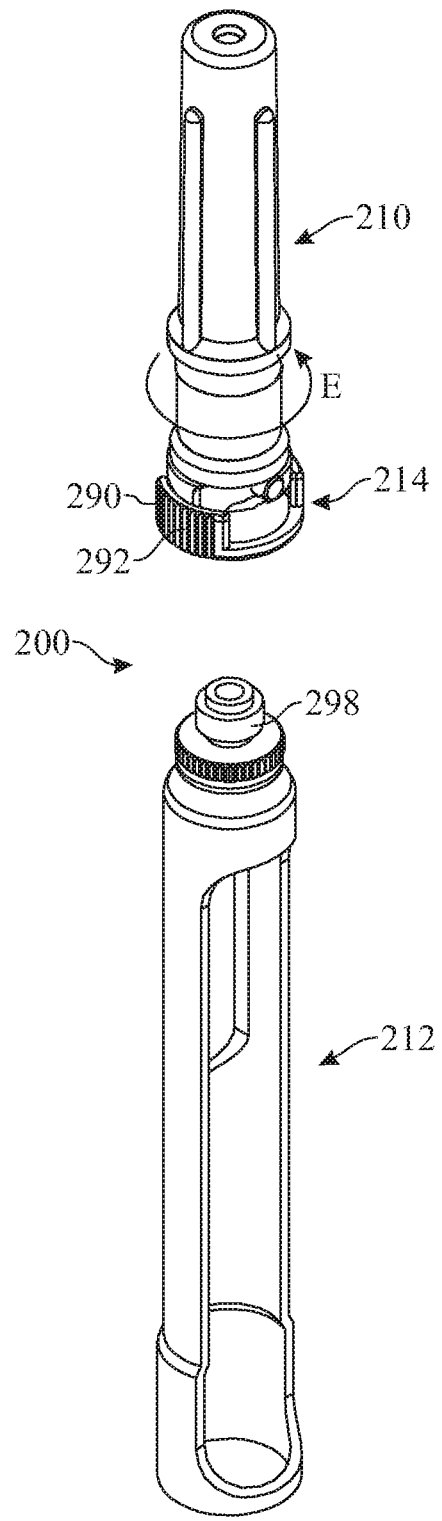
FIG. 11 presents a top side isometric view of the quick-connect syringe and needle system of FIG. 9, with the intermediate adapter shown connected to the needle assembly.
Figure 12:
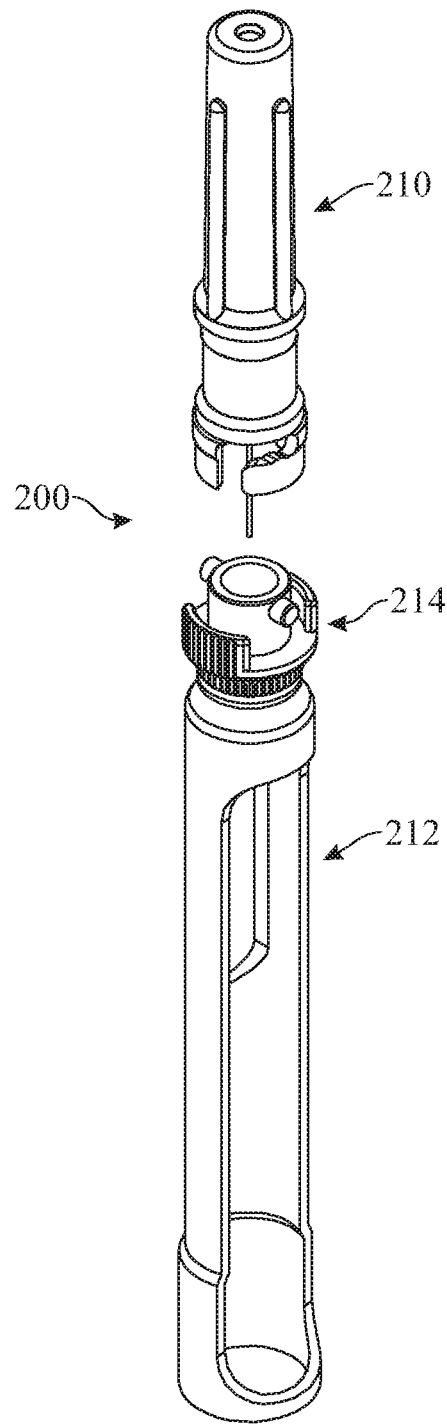
FIG. 12 presents a top front isometric view of the quick-connect syringe and needle system of FIG. 9, with the intermediate adapter shown connected to the syringe.
Figure 13:
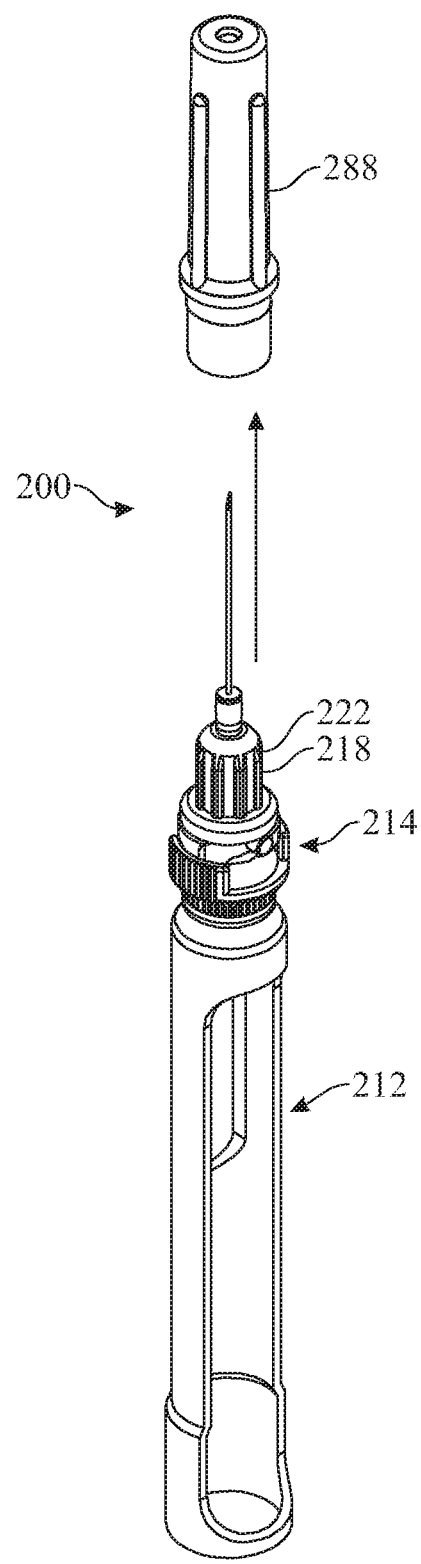
FIG. 13 presents a top front isometric view of the quick-connect syringe and needle system of FIG. 9, with the intermediate adapter and needle assembly body shown connected to the syringe and the cap removed from the needle assembly body.

As best shown in the exploded view of FIG. 10, the needle assembly 210 includes a needle assembly body 218 and a needle 216 affixed to the needle assembly body 218. The needle assembly body 218 comprises a forward portion 222 and a rear portion 224. Furthermore, the needle assembly 210 of the present embodiment includes a cap 288 which is detachably mountable on the forward portion 222 of the needle assembly body 218, as illustrated in FIG. 9, which shows the cap 288 mounted to the forward portion 222, and FIG. 13, which shows the cap 288 separated from the forward portion 222. As further shown in FIG. 10, the rear portion 224 of the needle assembly body 218 is formed as a slotted sleeve shaped and sized to fit over the front portion 246 of the intermediate adapter 214 when the quick-connect and needle system 200 is arranged in the assembled configuration. At least one slot 228 is defined through the slotted sleeve or rear portion 224. For instance and without limitation, two diametrically opposed slots 228 can be formed in the rear portion 224. The slots 228 can be L-shaped, comprising a first slot segment 276 having an open end at a rear end 280 of the rear portion 224 of the needle assembly body 218, and a second slot segment 278 extending from the first slot segment 276 and including a closed end 284. The first slot segment 276 of the L-shaped slot 228 can be parallel to the longitudinal axis 202, while the second slot segment 278 of the L-shaped slot 228 can be circumferential or arc-shaped about a center defined by the longitudinal axis 202.

With continued reference to FIG. 10, also similarly to the previous embodiment, the intermediate adapter 214 has a front portion 246 configured to connect to the needle assembly 210. Specifically, the front portion 246 includes at least one projection 250, such as two diametrically opposed projections 250, releasably engageable with the slot or slots 228 in the rear portion 224 of the needle assembly body 218 to disconnectably secure the intermediate adapter 214 to the needle assembly 210. Also similarly to the previous embodiment, the intermediate adapter 214 is engageable with the syringe 212; however, in the present embodiment, it is the front portion 246 that is disconnectably engageable with the syringe 212 to secure the intermediate adapter 214 to the syringe 212. Specifically, the front portion 246 of the body 242 of the intermediate adapter 214 includes an internal or female threaded portion 296 (FIG. 14) which threads to a forward, male threaded portion 298 of the syringe 212.

As further shown in FIG. 10, the intermediate adapter 214 additionally includes a radially-protruding collar 244 extending from the front portion 246, and an outer wall 290 disposed circumferentially about the longitudinal axis 202 of the intermediate adapter 214 in a spaced-apart relationship with the front portion 246. The outer wall 290 has an outer rugosity or texture 292 configured to provide a relatively high friction between the outer wall 290 and a user's fingers to facilitate manual application of a torque on the outer wall 290 and needle assembly 210 to rotate the needle assembly 210 and intermediate adapter 214 relative to one another. Thus, the user can grasp the outer wall 290 and easily rotate the needle assembly 210 and intermediate adapter 214 relative to one another to engage the one or more projections 250 of the front portion 246 of the intermediate adapter 214 with the one or more slots 228 of the rear portion 224 of the needle assembly body 218, as indicated by circular arrow E in the perspective view of FIG. 11.

Figure 14:
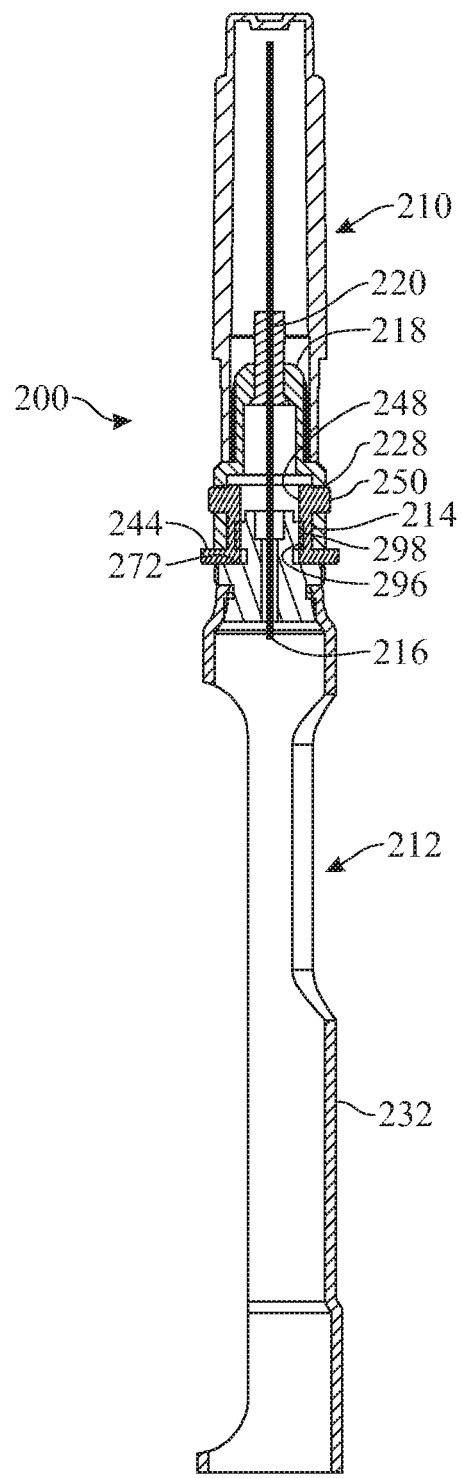
FIG. 14 presents a cross-sectional, side elevation view of the quick-connect syringe and needle system of FIG. 9 shown in the assembled configuration.

The quick-connect and needle system 200 of the present embodiment is configured to adopt an assembled configuration, shown in FIGS. 9 and 14. In the assembled configuration, the intermediate adapter 214 is secured to the syringe 212 by engagement of the front portion 246 of the intermediate adapter 214 with the syringe 212; more preferably, the intermediate adapter 214 is disconnectably secured to the syringe 212 by the threading of the forward, male threaded portion 298 of the syringe 212 into the female threaded portion 296 of the front portion 246 of the intermediate adapter 214. Also in this assembled configuration, the intermediate adapter 214 is disconnectably secured to the needle assembly 210 by engagement of the one or more projections 250 of the front portion 246 of the intermediate adapter 214 with the corresponding one or more slots 228 of the rear portion 224 of the needle assembly body 218 of the needle assembly 210. Furthermore, as best shown in FIG. 14, in the assembled configuration, the needle 216 extends through a through bore 248 of the intermediate adapter 214 and into the syringe 212, and the radially-protruding collar 244 of the intermediate adapter 214 rests on a front face 272 of the syringe 212. Furthermore, in the assembled configuration, the outer wall 290 of the intermediate adapter 214 is disposed radially outward of the rear portion 224 of the needle assembly body 218, as shown in FIG. 9.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A quick-connect syringe and needle system, comprising:
   a dental syringe, the dental syringe being configured to dispense an anesthetic from a carpule within the dental syringe;
   a needle assembly including a needle assembly body and a single needle affixed to the needle assembly body, the needle assembly body including a rear portion defining at least one slot and the single needle being configured to draw the anesthetic from the carpule for dispensing; and
   an intermediate adapter, the intermediate adapter including an internal threaded portion, the internal threaded portion engageable with the dental syringe to secure the intermediate adapter to the dental syringe, the intermediate adapter comprising at least one projection releasably engageable with the at least one slot in the rear portion of the needle assembly body to disconnectably secure the intermediate adapter to the needle assembly, and the intermediate adapter further comprising a through bore wherein the needle of the needle assembly extends through the through bore and into the syringe and a radially-protruding collar configured to rest on a front face of the dental syringe, the radially-protruding collar including an outer wall disposed circumferentially about a longitudinal axis of the intermediate adapter in a spaced apart relationship with a front portion of the intermediate adapter, the rear portion of the needle assembly engaging with the intermediate adapter between the front portion and the outer wall such that the outer wall covers the rear portion of the needle assembly; wherein
   the quick-connect and needle system is configured to adopt an assembled configuration in which the intermediate adapter is secured to the dental syringe, and further in which the intermediate adapter is disconnectably secured to the needle assembly by engagement of the at least one projection of the intermediate adapter with the at least one slot of the rear portion of the needle assembly body of the needle assembly, the outer wall of the intermediate adapter being disposed radially outward of the rear portion of the needle assembly body in the assembled configuration wherein the engagement of the intermediate adapter to the needle assembly forms a quick-connect mechanism in which the needle assembly is capable of being removed quickly from the dental syringe.

2. The quick-connect syringe and needle system of claim 1, wherein the rear portion of the needle assembly body comprises a slotted sleeve which fits over a front portion of the intermediate adapter when the quick-connect and needle system is arranged in the assembled configuration.

3. The quick-connect syringe and needle system of claim 2, wherein the at least one slot is defined through the slotted sleeve.

4. The quick-connect syringe and needle system of claim 3, wherein the at least one slot is L-shaped.

5. The quick-connect syringe and needle system of claim 4, wherein the L-shaped slot comprises a first slot segment having an open end, and a second slot segment extending from the first slot segment and including a closed end.

6. The quick-connect syringe and needle system of claim 5, wherein the first slot segment of the L-shaped slot is parallel to a longitudinal axis of the needle assembly.

7. The quick-connect syringe and needle system of claim 5, wherein the second slot segment of the L-shaped is circumferential about the longitudinal axis.

8. The quick-connect syringe and needle system of claim 1, wherein the at least one projection of the intermediate adapter comprises two projections and the at least one slot defined in the rear portion of the needle assembly body comprises two slots, and further wherein the two projections are configured to engage with the two slots.

9. The quick-connect syringe and needle system of claim 8, wherein the two projections are diametrically opposed to each other, and the two slots are diametrically opposed to one another.

10. The quick-connect syringe and needle system of claim 1, wherein the intermediate adapter is disconnectably engageable with the syringe.

11. The quick-connect syringe and needle system of claim 1, wherein the intermediate adapter comprises an outer wall disposed circumferentially about a longitudinal axis of the intermediate adapter, the outer wall comprising an outer texture facilitating manual application of a torque on the outer wall and needle assembly to rotate the needle assembly and intermediate adapter relative to one another for engaging the at least one projection of the intermediate adapter with the at least one slot of the rear portion of the needle assembly body of the needle assembly.

12. The quick-connect syringe and needle system of claim 11, wherein, when the quick-connect and needle system is arranged in the assembled configuration, the outer wall of the intermediate adapter is disposed radially outward of the rear portion of the needle assembly body.

13. A quick-connect syringe and needle system, comprising:
   a metallic dental syringe, the dental syringe being configured to dispense an anesthetic from a carpule within the dental syringe;
   a needle assembly including a needle assembly body and a single needle affixed to the needle assembly body, the needle assembly body including a rear portion defining at least one slot and the single needle being configured to draw the anesthetic from the carpule for dispensing; and
   an intermediate adapter, the intermediate adapter including an internal threaded portion, the internal threaded portion disconnectably threadable to a forward threaded portion of the dental syringe to secure the intermediate adapter to the dental syringe, the intermediate adapter comprising at least one projection releasably engageable with the at least one slot in the rear portion of the needle assembly body to disconnectably secure the intermediate adapter to the needle assembly, the intermediate adapter further comprising a through bore wherein the needle of the needle assembly extends through the through bore and into the syringe and a radially-protruding collar configured to rest on a front face of the dental syringe, the radially protruding collar including an outer wall disposed circumferentially about a longitudinal axis of the intermediate adapter in a spaced apart relationship with a front portion of the intermediate adapter, the rear portion of the needle assembly engaging with the intermediate adapter between the front portion and the outer wall such that the outer wall covers the rear portion of the needle assembly, the outer wall comprising an outer texture facilitating manual application of a torque on the outer wall and needle assembly to rotate the needle assembly and intermediate adapter relative to one another for engaging the at least one projection of the intermediate adapter with the at least one slot of the rear portion of the needle assembly body of the needle assembly; wherein the quick-connect and needle system is configured to adopt an assembled configuration in which the intermediate adapter is secured to the dental syringe by a threading of the intermediate adapter to the forward threaded portion of the dental syringe, and further in which the intermediate adapter is disconnectably secured to the needle assembly by engagement of the at least one projection of the intermediate adapter with the at least one slot of the rear portion of the needle assembly body of the needle assembly, the outer wall of the intermediate adapter being disposed radially outward of the rear portion of the needle assembly body in the assembled configuration, with the needle assembly body of the needle assembly extending through the through bore of the intermediate adapter and into the syringe, wherein the engagement of the intermediate adapter to the needle assembly forms a quick-connect mechanism in which the needle assembly is capable of being removed quickly from the dental syringe through a 90-degree turn.

\* \* \* \* \*